(12) United States Patent
Taylor et al.

(10) Patent No.: US 8,288,654 B2
(45) Date of Patent: *Oct. 16, 2012

(54) FEEDTHROUGH ASSEMBLY INCLUDING A FERRULE, AN INSULATING STRUCTURE AND A GLASS

(75) Inventors: William John Taylor, Anoka, MN (US); Brad C. Tischendorf, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 369 days.

This patent is subject to a terminal disclaimer.

(21) Appl. No.: 12/555,888

(22) Filed: Sep. 9, 2009

(65) Prior Publication Data
US 2009/0321107 A1 Dec. 31, 2009

Related U.S. Application Data

(63) Continuation-in-part of application No. 12/469,823, filed on May 21, 2009, now Pat. No. 8,129,622, which is a continuation-in-part of application No. 11/949,005, filed on Nov. 30, 2007.

(60) Provisional application No. 60/868,007, filed on Nov. 30, 2006.

(51) Int. Cl.
*H01B 17/26* (2006.01)

(52) U.S. Cl. .......... 174/152 GM; 174/50.59; 174/50.61; 65/59.1; 501/41; 501/49

(58) Field of Classification Search ........... 174/152 GM, 174/50.61, 50.64, 50.59; 501/78, 14, 11, 501/73, 77, 41, 49; 65/36, 59.1; 429/181, 429/180, 184, 185; 361/302, 320

See application file for complete search history.

(56) References Cited

U.S. PATENT DOCUMENTS

| | | |
|---|---|---|
| 3,646,405 A | 2/1972 | Wallis et al. |
| 3,803,875 A | 4/1974 | Root et al. |
| 3,920,888 A | 11/1975 | Barr |
| 4,152,540 A | 5/1979 | Duncan et al. |
| 4,285,730 A | 8/1981 | Sanford et al. |
| 4,314,031 A | 2/1982 | Sanford et al. |

(Continued)

FOREIGN PATENT DOCUMENTS

DE 8631853 U1 11/1988

(Continued)

OTHER PUBLICATIONS

Diemat DM2995PF Series Lead (Pb)-Free Sealing Glass Preforms—Preliminary Data Sheet, Aug. 27, 2006, 4 pages.

(Continued)

*Primary Examiner* — Angel R Estrada
*Assistant Examiner* — Dimary Lopez (57) ABSTRACT

A feedthrough assembly includes a ferrule, an insulating structure, at least one terminal pin and a glass seal that fixedly secures the insulating structure within the ferrule. The insulating structure has a top portion, a bottom portion, and an inner diameter portion. The inner diameter portion defines at least one aperture extending from the top portion to the bottom portion of the insulating structure. The at least one terminal pin extends through the at least one aperture. The glass seal comprises about 30% $B_2O_3$, about 30% to about 40% of a member selected from the group consisting of CaO, MgO, SrO, and combinations thereof, with the proviso that the individual amounts of CaO and MgO are each not greater than about 20%, about 5% $La_2O_3$, about 10% $SiO_2$, and about 15% $Al_2O_3$, wherein all percentages are mole percentages.

30 Claims, 4 Drawing Sheets

U.S. PATENT DOCUMENTS

| | | | |
|---|---|---|---|
| 4,323,654 | A | 4/1982 | Tick et al. |
| 4,420,569 | A | 12/1983 | Tick |
| 4,421,947 | A | 12/1983 | Kyle |
| 4,424,551 | A | 1/1984 | Stevenson et al. |
| 4,940,858 | A | 7/1990 | Taylor et al. |
| 4,943,686 | A | 7/1990 | Kucharek |
| 5,015,530 | A | 5/1991 | Brow et al. |
| 5,021,307 | A | 6/1991 | Brow et al. |
| 5,089,446 | A | 2/1992 | Cornelius et al. |
| 5,104,738 | A | 4/1992 | Brow et al. |
| 5,104,755 | A | 4/1992 | Taylor et al. |
| 5,175,067 | A | 12/1992 | Taylor et al. |
| 5,294,241 | A | 3/1994 | Taylor et al. |
| 5,306,581 | A | 4/1994 | Taylor et al. |
| 5,333,095 | A | 7/1994 | Stevenson et al. |
| 5,648,302 | A | 7/1997 | Brow et al. |
| 5,650,759 | A | 7/1997 | Hittman et al. |
| 5,693,580 | A | 12/1997 | Brow et al. |
| 5,817,984 | A | 10/1998 | Taylor et al. |
| 5,821,011 | A | 10/1998 | Taylor et al. |
| 5,825,608 | A | 10/1998 | Duva et al. |
| 5,851,222 | A | 12/1998 | Taylor et al. |
| 5,866,851 | A | 2/1999 | Taylor et al. |
| 5,867,361 | A | 2/1999 | Wolf et al. |
| 5,870,272 | A | 2/1999 | Seifried et al. |
| 5,871,513 | A | 2/1999 | Taylor et al. |
| 5,902,326 | A | 5/1999 | Lessar et al. |
| 5,922,444 | A * | 7/1999 | Tsuzuki et al. ............... 428/220 |
| 6,031,710 | A | 2/2000 | Wolf et al. |
| 6,076,017 | A | 6/2000 | Taylor et al. |
| 6,090,503 | A | 7/2000 | Taylor et al. |
| 6,275,369 | B1 | 8/2001 | Stevenson et al. |
| 6,349,025 | B1 | 2/2002 | Fraley et al. |
| 6,433,276 | B1 * | 8/2002 | Bellora ...................... 174/50.61 |
| 6,536,882 | B1 | 3/2003 | Hawkins et al. |
| 6,566,978 | B2 | 5/2003 | Stevenson et al. |
| 6,603,182 | B1 | 8/2003 | Low et al. |
| 6,643,903 | B2 | 11/2003 | Stevenson et al. |
| 6,660,116 | B2 | 12/2003 | Wolf et al. |
| 6,759,163 | B2 | 7/2004 | Frysz et al. |
| 6,759,309 | B2 | 7/2004 | Gross |
| 6,768,629 | B1 | 7/2004 | Allen et al. |
| 6,855,456 | B2 | 2/2005 | Taylor et al. |
| 6,888,233 | B2 | 5/2005 | Horning et al. |
| 6,924,165 | B2 | 8/2005 | Horning et al. |
| 7,046,499 | B1 | 5/2006 | Imani et al. |
| 7,094,967 | B2 | 8/2006 | Evans et al. |
| 7,098,117 | B2 | 8/2006 | Najafi et al. |
| 7,210,966 | B2 | 5/2007 | Taylor et al. |
| 7,214,441 | B2 | 5/2007 | Cortright et al. |
| 7,260,434 | B1 | 8/2007 | Lim et al. |
| 7,281,305 | B1 | 10/2007 | Iyer et al. |
| 7,285,509 | B2 | 10/2007 | Bayya et al. |
| 7,837,085 | B1 * | 11/2010 | Tziviskos ................... 228/122.1 |
| 7,964,523 | B2 * | 6/2011 | Mayumi et al. ................ 501/77 |
| 2001/0050837 | A1 | 12/2001 | Stevenson et al. |
| 2001/0055716 | A1 | 12/2001 | Frysz et al. |
| 2003/0083715 | A1 | 5/2003 | Taylor et al. |
| 2003/0123215 | A1 | 7/2003 | Allen et al. |
| 2003/0125185 | A1 | 7/2003 | Hirose |
| 2003/0179536 | A1 * | 9/2003 | Stevenson et al. ............ 361/302 |
| 2004/0126953 | A1 | 7/2004 | Cheung |
| 2004/0152229 | A1 | 8/2004 | Najafi et al. |
| 2004/0180464 | A1 | 9/2004 | Horning et al. |
| 2004/0244484 | A1 | 12/2004 | Horning et al. |
| 2005/0060003 | A1 | 3/2005 | Taylor et al. |
| 2005/0092507 | A1 | 5/2005 | Marshall et al. |
| 2005/0186823 | A1 | 8/2005 | Ring et al. |
| 2006/0009813 | A1 | 1/2006 | Taylor et al. |
| 2006/0173506 | A1 | 8/2006 | Rusin et al. |
| 2006/0192272 | A1 | 8/2006 | Receveur et al. |
| 2006/0247714 | A1 | 11/2006 | Taylor et al. |
| 2006/0290257 | A1 | 12/2006 | Heo et al. |
| 2007/0004580 | A1 | 1/2007 | Kass |
| 2007/0179554 | A1 | 8/2007 | Iyer et al. |
| 2007/0179555 | A1 | 8/2007 | Iyer et al. |
| 2007/0217121 | A1 | 9/2007 | Fu et al. |
| 2007/0234540 | A1 * | 10/2007 | Iyer et al. ..................... 29/25.42 |
| 2007/0239223 | A1 | 10/2007 | Engmark et al. |
| 2007/0260282 | A1 | 11/2007 | Taylor et al. |
| 2008/0060844 | A1 | 3/2008 | Teske et al. |
| 2008/0118831 | A1 * | 5/2008 | Jouanneau-Si-Larbi et al. ............................ 429/188 |
| 2009/0079517 | A1 | 3/2009 | Iyer |
| 2009/0079518 | A1 | 3/2009 | Iyer |
| 2009/0079519 | A1 | 3/2009 | Iyer |

FOREIGN PATENT DOCUMENTS

| | | |
|---|---|---|
| EP | 0404435 A1 | 12/1990 |
| EP | 0404435 B1 | 9/1996 |

OTHER PUBLICATIONS

Diemat DM2700PF Series, DM2700PF/DM2760PF, Low-Temperature Sealing Glass Preforms—Product Data Sheet, Jul. 24, 2006, 4 pages.

Diemat, Inc. Material Safety Data Sheet—DM2995PF, Aug. 23, 2006, 4 pages.

International Search Report for PCT/US2009/050191 dated Oct. 6, 2009, 4 pages.

International Search Report for PCT/US2008/077179 dated May 25, 2009, 4 pages.

Yourassowsky, E. et al., Combination of minocycline and rifampicin against methicillin- and gentamicin-resistant *Staphylococcus aureus*, J Clin Pathol 1981; 34:559-563.

Bayston, R. et al., Antimicrobial activity of silicone rubber used in hydrocephalus shunts, after impregnation with antimicrobial substances, J Clin Pathol 1981; 34:1057-1062.

(PCT/US2010/048086) PCT Notification of Transmittal of the International Search Report and the Written Opinion of the International Searching Authority, Dec. 20, 2010.

* cited by examiner

FEEDTHROUGH ASSEMBLY INCLUDING A FERRULE, AN INSULATING STRUCTURE AND A GLASS

CROSS-REFERENCE TO RELATED APPLICATIONS

This application is a continuation-in-part of U.S. patent application Ser. No. 12/469,823 filed on May 21, 2009, which is a continuation-in-part of U.S. patent application Ser. No. 11/949,005 filed on Nov. 30, 2007, which claims the benefit of U.S. Provisional Application No. 60/868,007, filed on Nov. 30, 2006. The entire disclosures of each of the above applications are incorporated herein by reference.

FIELD

The present disclosure relates generally to construction of a feedthrough assembly for use in an implantable medical device (IMD), and more particularly, to insulating glass within the feedthrough assembly.

BACKGROUND

This section provides background information related to the present disclosure that is not necessarily prior art.

Numerous devices (e.g., implantable medical devices (IMDs), electrochemical cells (e.g., batteries, capacitors, or sensors) are hermetically sealed to prevent liquid from contacting electronic components within the device. A typical feedthrough assembly consists of a conductive element (e.g., wires or pins), a ferrule or sleeve member, an insulating member (e.g., glass, ceramic), and a seal. Feedthroughs include those described in U.S. Pat. Nos. 6,855,456 and 5,175,067 and U.S. Pat. App. Pub. No. 2006/0247714, all to Taylor et al. The ferrule or sleeve member includes an aperture configured to receive the insulating member. A seal may be located between the ferrule or sleeve member and the insulating member. Insulating members include those formed of Ta-23 glass and Cabal-12 glass, as described in U.S. Pat. No. 5,306,581 to Taylor et al. An exemplary feedthrough assembly may be inserted, for example, into a housing of a battery such that a portion of the conductive element extends into the housing to connect with battery elements while another portion of the conductive element extends outside of the housing to connect with other electronic components.

Construction of a feedthrough assembly can require the use of forming weights, complicating production, and in some instances, limiting the minimum feedthrough size. In addition, some insulating members are susceptible to reaction with aqueous solutions, such as body fluids. Reaction with body fluids can erode the insulating member and diminish performance over time. It is desirable to develop improved feedthroughs for IMDs.

SUMMARY

This section provides a general summary of the disclosure, and is not a comprehensive disclosure of its full scope or all of its features.

Glass insulating members and glass preforms are provided that comprise about 30% $B_2O_3$; about 30% to about 40% of a member selected from the group consisting of CaO, MgO, SrO, and combinations thereof, with the proviso that the individual amounts of CaO and MgO are each not greater than about 20%; about 5% $La_2O_3$; about 10% $SiO_2$; and about 15% $Al_2O_3$, wherein all percentages are mole percentages. These insulating members and preforms are used in feedthrough assemblies and methods of forming feedthrough assemblies.

According to various embodiments of the present disclosure, a feedthrough assembly includes a ferrule, an insulating structure, and a glass seal that fixedly secures the insulating structure within the ferrule. The glass seal comprises about 30% $B_2O_3$, about 30% to about 40% of a member selected from the group consisting of CaO, MgO, SrO, and combinations thereof, with the proviso that the individual amounts of CaO and MgO are each not greater than about 20%, about 5% $La_2O_3$, about 10% $SiO_2$, and about 15% $Al_2O_3$, wherein all percentages are mole percentages.

According to various embodiments of the present disclosure, a method of manufacturing a feedthrough assembly includes providing a ferrule and inserting an insulating structure within the ferrule. The method further includes forming a glass seal that fixedly secures the insulating structure within the ferrule. The glass seal comprises about 30% $B_2O_3$, about 30% to about 40% of a member selected from the group consisting of CaO, MgO, SrO, and combinations thereof, with the proviso that the individual amounts of CaO and MgO are each not greater than about 20%, about 5% $La_2O_3$, about 10% $SiO_2$, and about 15% $Al_2O_3$, wherein all percentages are mole percentages.

According to various embodiments of the present disclosure, a feedthrough assembly includes a ferrule, an insulating structure, at least one terminal pin and a glass seal that fixedly secures the at least one terminal pin with the insulating structure. The insulating structure has a top portion, a bottom portion, and an inner diameter portion. The inner diameter portion defines at least one aperture extending from the top portion to the bottom portion of the insulating structure. The at least one terminal pin extends through the at least one aperture. The glass seal comprises about 30% $B_2O_3$, about 30% to about 40% of a member selected from the group consisting of CaO, MgO, SrO, and combinations thereof, with the proviso that the individual amounts of CaO and MgO are each not greater than about 20%, about 5% $La_2O_3$, about 10% $SiO_2$, and about 15% $Al_2O_3$, wherein all percentages are mole percentages.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. In addition, disclosure of ranges includes disclosure of all distinct values and further divided ranges within the entire range.

Further areas of applicability will become apparent from the description provided herein. The description and specific examples in this summary are intended for purposes of illustration only and are not intended to limit the scope of the present disclosure.

DRAWINGS

Example embodiments will now be described more fully with reference to the accompanying drawings.

DETAILED DESCRIPTION

One embodiment of the invention involves a feedthrough assembly in a microelectromechanical system (MEMS) package. The conductive hermetic feedthrough connects an interior cavity in the MEMS device to another electronic component or device (e.g., lead interconnect) outside of the MEMs package. The MEMS package may be hermetic and isolated from body fluid contact more so than packages that employ an epoxy attachment to a silicon substrate.

Figure 1:
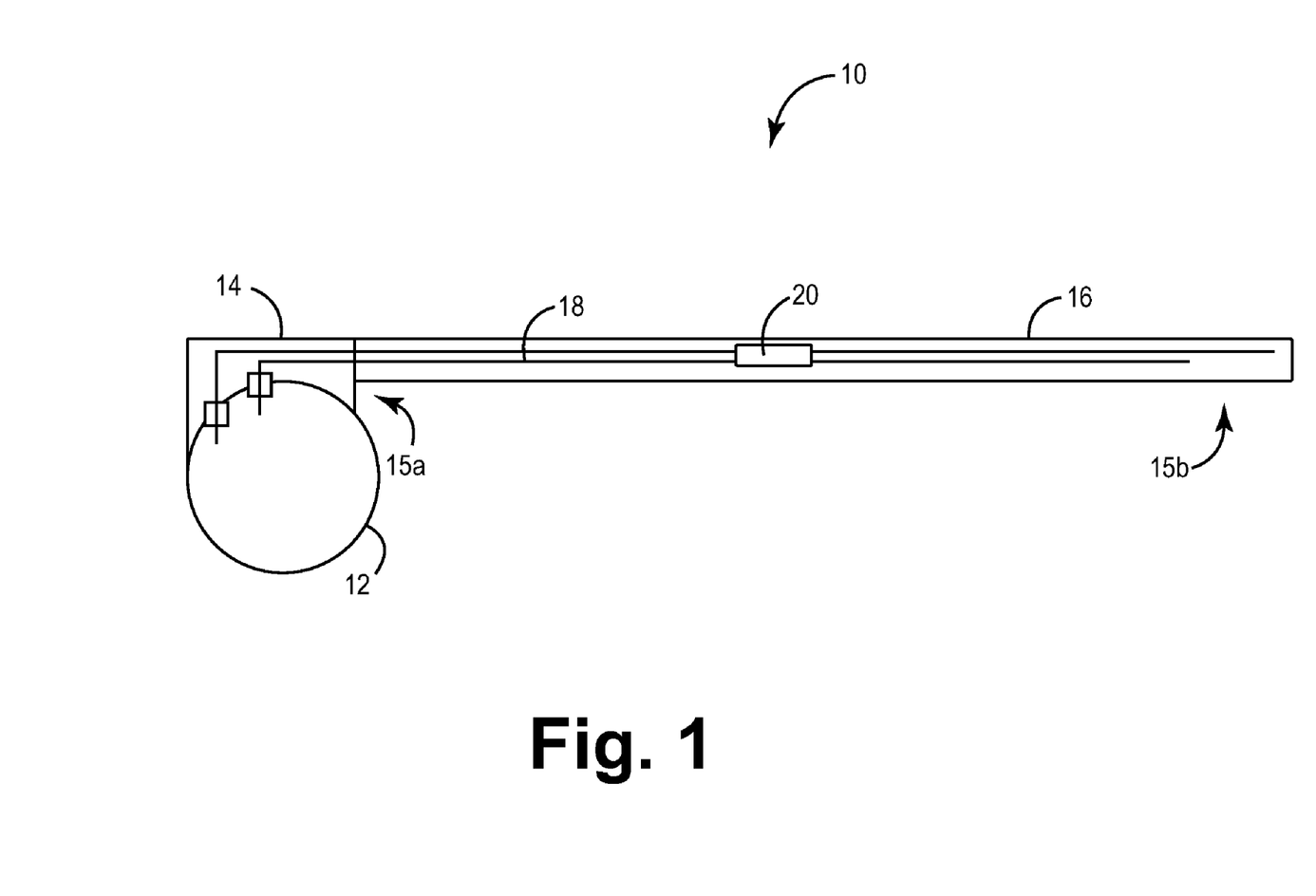
FIG. 1 depicts a schematic view of an implantable medical device.

FIG. 1 depicts a functional unit 20 in a medical device system 10. Functional unit 20 includes a feedthrough assembly (not shown) on or in an integrated circuit (IC), a substrate that includes electronic components (e.g., transistors, logic gates, switches), or a substrate alone. Functional unit 20 can be used anywhere outside the medical device 12 and may be electrically connected to one or more conductor(s) 18. For example, functional unit 20 can serve as a sensor (e.g., pressure sensor) that employs a feedthrough assembly.

Medical device system 10 includes a medical device housing 12 having a connector module 14 that electrically couples various internal electrical components of medical device housing 12 to a proximal end 15a of a medical lead 16 such as one or more conductors 18 (e.g., coil, wire) that extend to a distal end 15b of lead 16. Medical device system 10 may comprise any of a wide variety of medical devices that include one or more medical lead(s) 16 and circuitry coupled to the medical lead(s) 16. By way of example, medical device system 10 may take the form of an implantable cardiac pacemaker that provides therapeutic stimulation to the heart or a neurostimulator. Alternatively, medical device system 10 may take the form of an implantable cardioverter, an implantable defibrillator, an implantable cardiac pacemaker-cardioverter-defibrillator (PCD), an implantable pulse generator, or an implantable medical device that solely monitors conditions associated with the patient.

Figure 2:
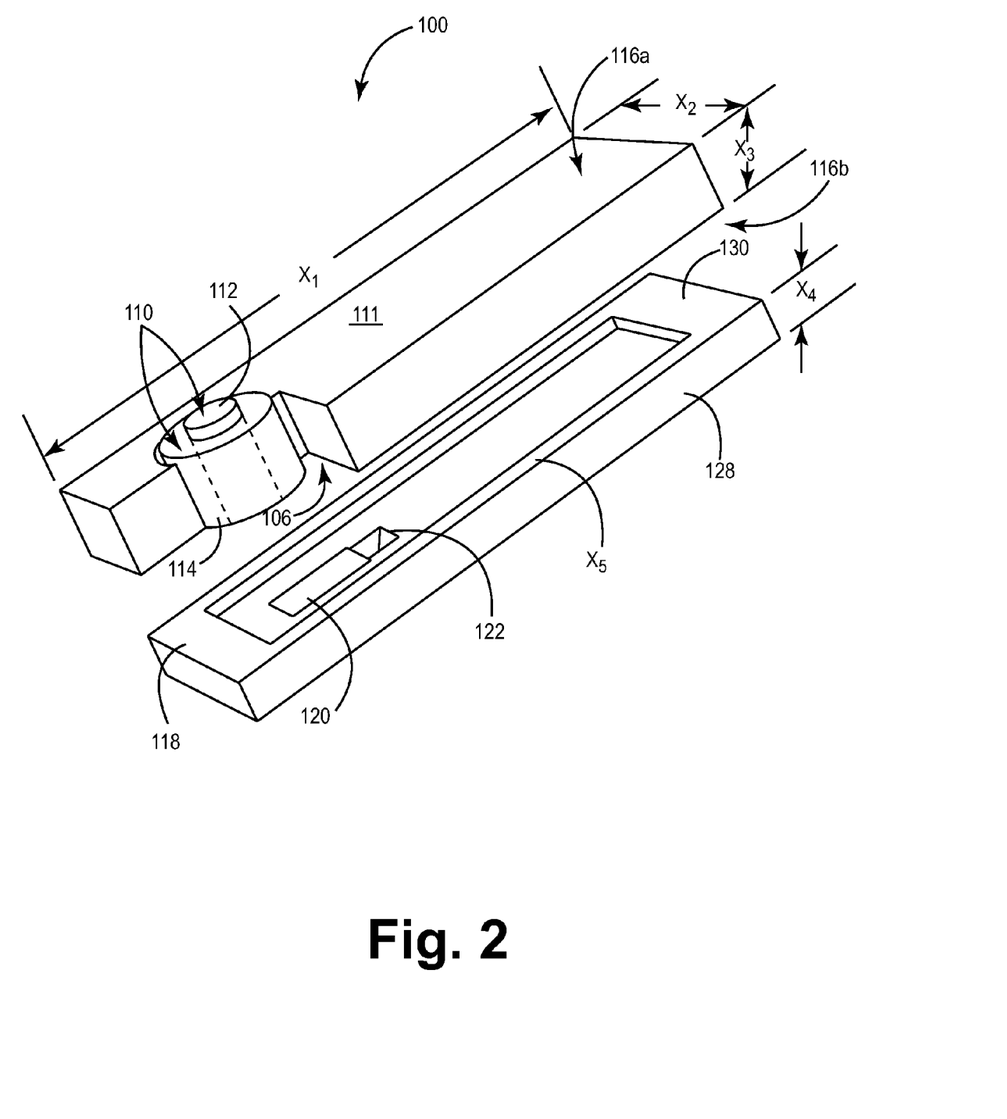
FIG. 2 is a schematic cut away view of a MEMS package that includes a feedthrough assembly.

FIG. 2 illustrates one embodiment of a MEMS package 100 for medical device system 10. MEMS package 100, in one embodiment, may be used in or for a sensor. For example, a MEMS package 100 could be associated with a transducer, which converts a signal into an electrical signal (i.e., voltage, current).

MEMS package 100 includes a feedthrough assembly 110, a first substrate 111, and a second substrate 128. Feedthrough assembly 110 may be hermetically disposed in an aperture 106 of first substrate 111, and coupled to second substrate 128. Feedthrough assembly 110 (e.g., glass-pin-insulator seal) comprises a conductive element 112 (e.g., pin) hermetically housed in an insulating member 114 (also referred to as sealing glass). Conductive element 112 may be formed of a conductive material, such as tantalum (Ta), niobium (Nb), titanium (Ti), platinum (Pt), iridium (Ir) and/or alloys thereof.

Insulating member 114 may be formed of glass. Typical glass for formation of insulating member 114 comprises boro-alumino, boro-alumino silicate and/or boro silicate type glasses with a wide range of thermal expansions to approximately match biostable conductive element 112 materials such as Ta, Nb, niobium-titanium (Nb—Ti) alloy, Pt, Pt alloys, Ti, alloys of Ti and/or other suitable materials. The element(s) and/or compounds used to form insulating member 114 are selected in a manner to reduce tensile stresses with conductive element 112. For example, insulating member 114, employing glass, has a CTE value about equivalent to or within 15% of the CTE associated with conductive element 110.

The insulating member 114 may be formed from a glass preform. For example, in making a feedthrough assembly 110, the glass preform may be melted so that the molten glass engages conductive element 112 and the inner walls of aperture 106 and subsequently cooled to form insulating member 114. The glass preform has a composition comprising about 30-40% $B_2O_3$, about 0-20% CaO, about 0-20% MgO, about 0-20% SrO, about 0-5% $La_2O_3$, about 5-10% $SiO_2$, and about 10-20% $Al_2O_3$, where all percentages represent mole percents. In some embodiments, the composition further comprises up to about 10% of $MnO_2$, and in some cases the $MnO_2$ may be about 15%. In some embodiments, all or some of the amounts of CaO and/or MgO are replaced with a corresponding amount of SrO, where the amount of SrO does not exceed about 40%. For example, about 10% of CaO and about 5% MgO may be replaced with about 15% SrO. However, the amounts of CaO and MgO are not entirely replaced by SrO, and none of CaO, MgO, and SrO is above 30%. In some embodiments, the composition includes about 30% $B_2O_3$, about 20% CaO, about 20% MgO, about 5% $La_2O_3$, about 10% $SiO_2$, and about 15% $Al_2O_3$.

Various components of the glass composition provide benefits in making a feedthrough assembly 110 and provide the resulting insulating member 114 with advantageous properties. In particular, $La_2O_3$ provides for better glass flow in melting and forming the insulating member 114, as lower temperatures may be employed compared to glass without $La_2O_3$ or with less $La_2O_3$. Lanthanum oxide also increases the coefficient of thermal expansion (CTE) value of the glass. For example, glass with little or no lanthanum oxide may have a CTE of about 6.5, where glass with lanthanum oxide as described herein may have a CTE of about 8.0. The increased CTE values are closer to the CTE values for metals, such as niobium (Nb), titanium (Ti), platinum (Pt), iridium (Ir) and/or alloys thereof. Similar CTE values alter the resulting compressive force applied to the glass insulating member when disposed within a ferrule (not shown) or the inner walls of aperture 106 upon forming and cooling the feedthrough assembly 110. Excessive tensile force can be caused by this alteration, which can cause tensile cracks in the glass insulating member 114. The propensity for such tensile cracks may be reduced by employing the present compositions. For example, the present compositions may provide CTE values that are about 10-15% less than the metal of the inner walls of aperture 106 or of a ferrule.

Strontium oxide within the composition also lowers the processing temperature. For example, as described above, all or some of the amounts of CaO and/or MgO may be replaced with a corresponding amount of SrO. In this way, the processing temperature of the glass composition may be adjusted, for example, in order to offset temperatures necessary to process amounts of silicon dioxide.

The present composition also limits the amount of $SiO_2$ to about 10%, as this amount provides long-term durability but does not substantially increase the processing temperature. For example, $SiO_2$ in the range of 20% or more increases the temperature required for processing the glass to the point where titanium, which can be used, for example, in conductive element 112, as part of a ferrule, or in the first substrate 111, undergoes a phase transition. This may cause titanium parts, or other metal parts approaching the respective metal or alloy melting temperature, to subsequently warp or become distorted. Thus, the present glass composition keeps the amount of silicon dioxide amount low to allow lower processing temperatures where integrity of titanium portion(s) of the feedthrough assembly 110 are maintained.

The present glass compositions also provide advantageous bonding and sealing between the insulating member 114 and the inner walls of aperture 106 and between the insulating member 114 and conductive element 112. In other embodiments, described below, the glass composition provides bonding and sealing to a ferrule. The present glass compositions may be used to replace glass insulating members used in feedthroughs as described in U.S. Pat. Nos. 6,855,456; 5,306,581; 5,175,067; and 4,940,858; and in U.S. Pat. App. Pub. No. 2006/0247714, all to Taylor et al., as well as U.S. Pat. No. 5,902,326 to Lessar et al., the disclosures of which are each incorporated herein by reference in their entirety.

Conductive element 112 and first substrate 111 are hermetically joined by the insulator material (e.g., glass) of insulating member 114 flowing and engaging conductive element 112 and the inner walls of aperture 106. The hermetic seal could be a coefficient of thermal expansion (CTE) value match, or an approximate match (e.g., CTE within 10%) for all MEMS package components. In another embodiment, the CTE may be within 5% for all MEMS package components. In another embodiment, the CTE may be within 2.5% for all MEMS package components. In yet another embodiment, first substrate 111 (e.g., housing) possesses a CTE greater than insulating member 114 and conductor 112, thereby forming a compression seal.

The present disclosure also provides methods of forming a feedthrough assembly 110. A glass preform may be positioned around a portion of an electrically conductive element 112. The glass preform may comprise the compositions as described herein. At least a portion of the glass preform may be positioned within an aperture 106 of a substrate 111 or within a sleeve member. The glass preform may be softened or fully melted to form a glass insulating member 114 having a sealing engagement with the electrically conductive element 112 and having a sealing engagement with the aperture 106 of the substrate 111 or the sleeve member. In some embodiments, softening or fully melting the glass preform to form a glass insulating member 114 having a sealing engagement with the electrically conductive element 112 and having a sealing engagement with the aperture 106 of the substrate 111 or the sleeve member does not require the use of one or more forming weights. In some embodiments, softening or fully melting the glass preform does not cause the electrically conductive element 112 to undergo a phase transition and does not cause the substrate 111 or the sleeve member to undergo a phase transition, preventing these components from becoming warped or distorted.

First substrate 111 includes a first surface 116a (also referred to as ceramic or glass housing material), a second surface 116b (e.g., silicon material), length X1, width X2, thickness X3, and an aperture 106 for receiving feedthrough assembly 110. First substrate 111 contains the hermetic seal feedthrough assembly 110 and metallized tracings for establishing an electrical connection to second substrate 128. In one embodiment, first substrate 111 comprises a ceramic or glass having a coefficient thermal expansion (CTE) value equivalent to or greater than feedthrough 110 (e.g., pin/glass assembly).

In one embodiment, first substrate 111 may be comprised of a material that has about an equivalent or greater CTE value than conductive element 112 and glass insulating member 114. First substrate 111 can include a ceramic such as for example, polycrystalline alumina with a CTE of about 8.0, sapphire (e.g., single crystal alumina) with a CTE of about 8.0, and zirconia with a CTE of about 10. In another embodiment, first substrate 111 or housing may be made of glass instead of a ceramic, and possesses general characteristics such that (1) the glass has a higher melting point than insulating member 114; and/or (2) the glass has about an equivalent or greater CTE value than the sealing glass.

Second substrate 128 includes via 122, a metallized trace 120 and includes electronic components that allow MEMS package 110 to function as a sensor substrate such as a transducer; however, skilled artisans appreciate that the substrate may be configured to include any type of circuitry such as switches, signal processing capability, and/or any other suitable form of circuitry related to an implantable medical devices. Second substrate 128 possesses about the same or similar dimensions as first substrate 111. For example, thickness X4 may be the same or about the same as X3. Wall thickness X5 forms a perimeter on the first surface 130 of second substrate 128. The second surface (not shown) of second substrate 128 may be directly adjacent to the housing of an implantable medical device.

Feedthrough assembly 110, disposed in first substrate 111, may then be coupled through joint 118 (e.g., a frit joint) to second substrate 128 (also referred to as a silicon MEMS substrate). Coupling of first substrate 111 to the second substrate 128 may be achieved by use of a glass frit, an Au-silicon eutectic material or other suitable material 118. Second substrate 128 (silicon) material generally has a higher melting point than the glass used to create to a glass insulating member 114. Conductive element 110 may be electrically connected to second substrate 128 through a metal tracing 120. In one embodiment, the metal tracing 120 may be located, for example, in second substrate 128.

Table 1, presented below, provides exemplary dimensions for components of MEMS package 100; however, skilled artisans appreciate that other dimensions may also be used.

TABLE 1

Exemplary dimensions for components of MEMS package.

| Component | Dimension millimeters (mm) |
| --- | --- |
| Conductive element 112 diameter | 0.40 |
| Glass insulating member 114 diameter | 0.75 |
| length X1 | 3.50 |
| width X2 | 1.00 |
| thickness X3 | 0.40 |
| thickness X4 | 0.25 |
| Wall X5 | 0.25 |

Skilled artisans understand other embodiments may implement the principles described herein. For example, a functional unit 20 may be placed in a free body such as a lead. Additionally, while MEMS package is described relative to a sensor or a sensor component (e.g., transducer), it is contemplated that MEMS package 100 can be used in a variety of ways to achieve certain functions of implantable medical devices.

Figure 3:
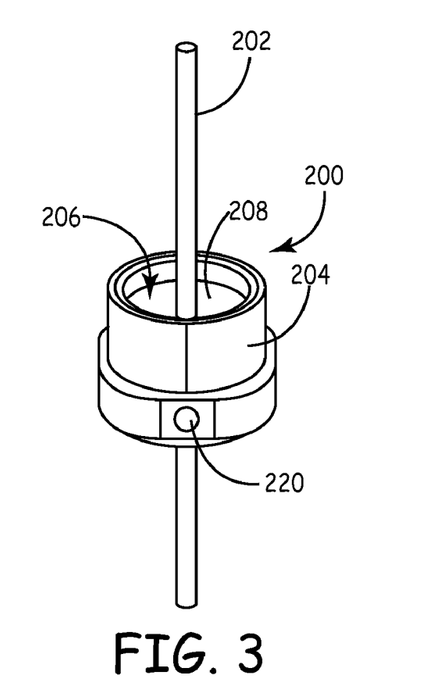
FIGS. 3 and 4 are isometric and cross-sectional views, respectively, of a unipolar (single pin) feedthrough assembly according to various embodiments of the present invention.
Figure 4:
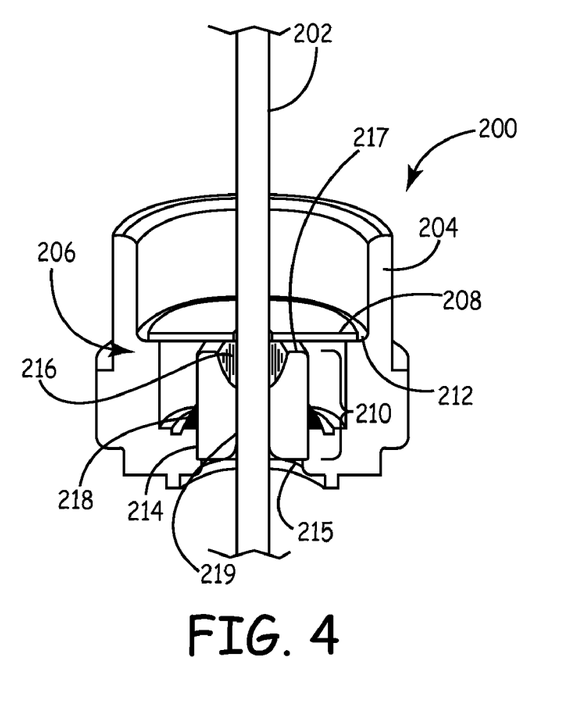

FIGS. 3 and 4 are isometric and cross-sectional views, respectively, of a unipolar (single pin) feedthrough assembly 200 having a terminal pin 202 extending therethrough. It should be understood, however, that the teachings of the present disclosure can be applied to feedthrough assemblies that include multiple terminal pins, as well as those that do not include terminal pins. Feedthrough assemblies that do not include terminal pins, such as those described in U.S. Pat. No. 5,902,326, are sometimes referred to as "optical" feedthroughs.

Assembly 200 comprises a generally cylindrical ferrule 204 having a cavity through which pin 202 passes. Ferrule 204 is made of an electrically conductive material (e.g., titanium alloy) and is configured to be fixedly coupled (e.g., welded) to the container of a device to be hermetically sealed, such as a medical device. An insulating structure 206 is disposed within ferrule 204 to secure pin 202 relative to ferrule 204 and to electrically isolate pin 202 from ferrule 204. Insulating structure 206 comprises a supporting structure 208 and a joint-insulator sub-assembly 210, both of which are disposed around terminal pin 202. In various embodiments, supporting structure 208 may be absent from insulating structure 206. As will be more fully described below, joint-insulator sub-assembly 210 acts as an insulative seal and can take the form of, for example, a braze joint or glass seal. Supporting structure 208 can be made of a non-conductive material (e.g., polyimide) and rests on an inner ledge 212 provided within ferrule 204.

As can be seen in FIG. 4, joint-insulator sub-assembly 210 comprises three main components: an insulator ring 214 (e.g., made from a ceramic material) that insulates pin 202 from ferrule 204, a pin-insulator seal 216 (e.g., made from gold braze or glass seal) that couples insulating ring 214 to pin 202, and an insulator-ferrule seal 218 (e.g., made from gold braze or glass seal) that couples insulating ring 214 to ferrule 204. The insulator ring 214 can include a bottom portion 215, a top portion 217 and an inner diameter portion 219. The inner diameter portion 219 defines an aperture through which terminal pin 202 can extend.

In various embodiments of the present disclosure, one or both of the pin-insulator seal 216 and the insulator-ferrule seal 218 can be formed of the glass composition described above. That is, the pin-insulator seal 216 and the insulator-ferrule seal 218 can be glass having a composition comprising about 30-40% $B_2O_3$, about 0-20% CaO, about 0-20% MgO, about 0-20% SrO, about 0-5% $La_2O_3$, about 5-10% $SiO_2$, and about 10-20% $Al_2O_3$, where all percentages represent mole percents. In some embodiments, the composition further comprises up to about 10% of $MnO_2$, and in some cases the $MnO_2$ may be about 15%. In some embodiments, all or some of the amounts of CaO and/or MgO are replaced with a corresponding amount of SrO, where the amount of SrO does not exceed about 40%. For example, about 10% of CaO and about 5% MgO may be replaced with about 15% SrO. However, the amounts of CaO and MgO are not entirely replaced by SrO, and none of CaO, MgO, and SrO is above 30%. In some embodiments, the composition includes about 30% $B_2O_3$, about 20% CaO, about 20% MgO, about 5% $La_2O_3$, about 10% $SiO_2$, and about 15% $Al_2O_3$.

Joint-insulator sub-assembly 210 is exposed along the underside of ferrule 204. When ferrule 204 is fixedly coupled to the container of a medical device, for example, the lower portion of ferrule 204, and thus the lower portion of joint-insulator sub-assembly 210, can be exposed to body fluids. For this reason, it is important that joint-insulator sub-assembly 210 forms a hermetic seal between ferrule 104 and terminal pin 202. Joint-insulator sub-assembly 210 can be leak tested. To permit this test to be performed, an aperture 220 (FIG. 3) is provided through ferrule 204 to the inner annular cavity formed by the outer surface of joint-insulator sub-assembly 210, the lower surface of supporting structure 208, and the inner surface of ferrule 204. A gas is delivered through aperture 220 into the inner annular cavity, and aperture 220 is plugged. Preferably, a gas of low molecular weight (e.g., helium or hydrogen) is chosen so that it can easily penetrate small cracks in joint-insulator sub-assembly 210. Feedthrough 200 is then monitored for the presence of the gas proximate joint-insulator sub-assembly 210 by way of, for example, a mass spectrometer. If no gas is detected, it is concluded that joint-insulator sub-assembly 210 has formed a satisfactory seal.

Figure 5:
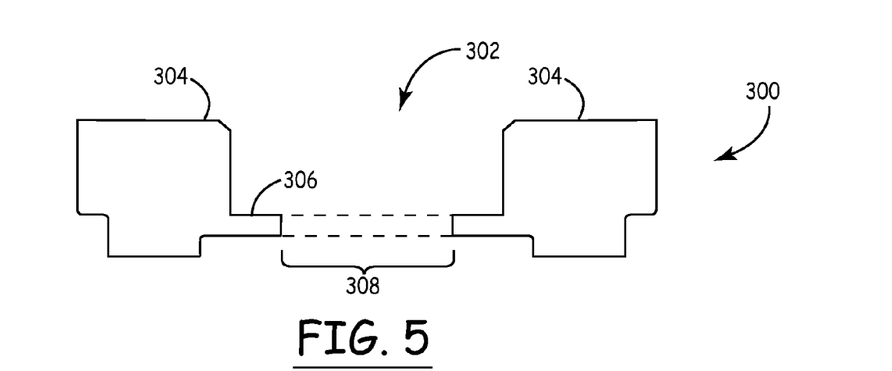
FIGS. 5-7 illustrate a method of manufacturing an exemplary feedthrough assembly according to various embodiments of the present disclosure.
Figure 6:
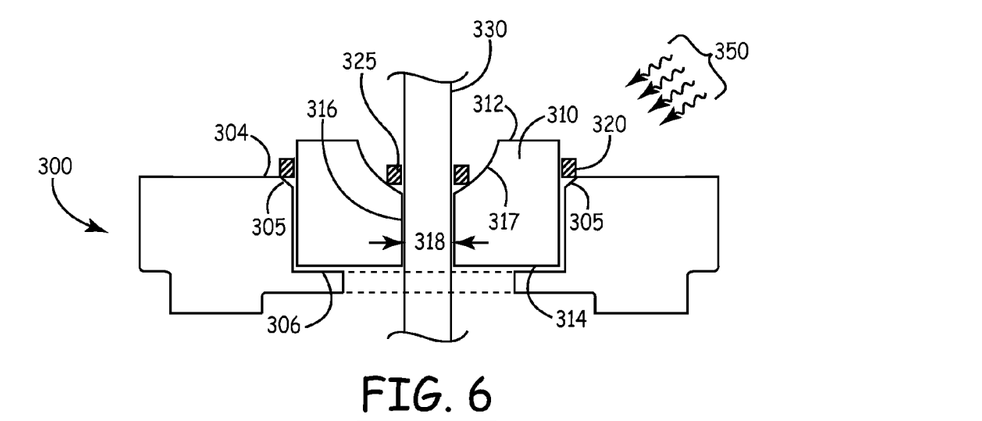
Figure 7:
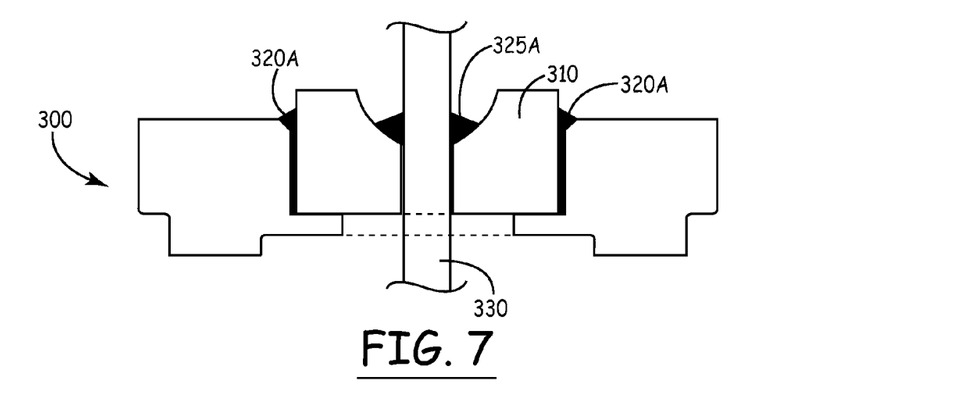

Referring now to FIGS. 5-7, a method of manufacturing an exemplary feedthrough assembly according to various embodiments of the present disclosure is illustrated. A ferrule 300 can include a recessed portion 302 in which an insulating structure 310 can be inserted. The recessed portion 302 can be bordered by wall portions 304 and further include a ledge 306 upon which an inserted insulating structure 310 can be placed such that the insulating structure 310 abuts the ledge 306. The recessed portion 302 can also define an opening 308 through which a terminal pin 330 can extend.

Insulating structure 310 can include a top portion 312, a bottom portion 314 and an inner diameter portion 316 that defines an aperture 318 that extends from the top portion 312 to the bottom portion 314. In various embodiments, insulating structure 310 can include an angled portion 317 that assists with the bonding of the terminal pin 330 with insulating structure 310, as described more fully below.

In various embodiments of the present disclosure, the insulating structure 310 is inserted into the recessed portion 302 and the terminal pin 330 is inserted into aperture 318. A glass preform 320 can be fitted around insulating structure 310, and a second glass preform 325 can be fitted around terminal pin 330. In various embodiments, a chamfer 305 can be included in wall portions 304 to more securely position the glass preform 320 adjacent insulating structure 310. Further, angled portion 317 can be included in the insulating structure to more securely position the glass preform 325 adjacent terminal pin 330.

Upon application of heat 350, glass preform 320 will soften or partially or completely melt and flow into the recessed portion 302 between insulating structure 310 and wall portions 304. In this manner, glass preform 320 will form a glass seal 320A that fixedly secures the insulating structure 310 to ferrule 300, as illustrated in FIG. 7. Different types of energy (e.g., radiation, microwave, magnetic) can be utilized instead of, or in addition to, heat 350, depending on the composition of the preform utilized. The same or similar method can be utilized to create glass seal 325A between terminal pin 330 and insulating structure 310. The use of one of glass seals 320A, 325A in combination with a gold braze or other sealing compositions (such as, glass seal 320A utilized with a gold braze utilized to seal terminal pin 330 with insulating structure 310, or glass seal 325A utilized with a gold braze utilized to seal ferrule 300 with insulating structure 310) is within the scope of the present disclosure.

In various embodiments of the present disclosure, the glass preforms 320, 325 and glass seals 320A, 325A can be formed of the glass composition described above. That is, the glass preforms 320, 325 and glass seals 320A, 325A can be glass having a composition comprising about 30-40% $B_2O_3$, about 0-20% CaO, about 0-20% MgO, about 0-20% SrO, about 0-5% $La_2O_3$, about 5-10% $SiO_2$, and about 10-20% $Al_2O_3$, where all percentages represent mole percents. In some embodiments, the composition further comprises up to about 10% of $MnO_2$, and in some cases the $MnO_2$ may be about 15%. In some embodiments, all or some of the amounts of CaO and/or MgO are replaced with a corresponding amount of SrO, where the amount of SrO does not exceed about 40%. For example, about 10% of CaO and about 5% MgO may be replaced with about 15% SrO. However, the amounts of CaO and MgO are not entirely replaced by SrO, and none of CaO, MgO, and SrO is above 30%. In some embodiments, the composition includes about 30% $B_2O_3$, about 20% CaO, about 20% MgO, about 5% $La_2O_3$, about 10% $SiO_2$, and about 15% $Al_2O_3$.

The broad teachings of the disclosure can be implemented in a variety of forms. Therefore, while this disclosure includes particular examples, the true scope of the disclosure should not be so limited since other modifications will become apparent upon a study of the drawings, the specification, and the following claims.

What is claimed is:

1. A feedthrough assembly, comprising:
   a ferrule;
   an insulating structure; and
   a glass seal fixedly securing the insulating structure within the ferrule, the glass seal comprising:
      about 30% $B_2O_3$;
      about 30% to about 40% of a member selected from the group consisting of CaO, MgO, SrO, and combinations thereof, with the proviso that the individual amounts of CaO and MgO are each not greater than about 20%;
      about 5% $La_2O_3$;
      about 10% $SiO_2$; and
      about 15% $Al_2O_3$,
      wherein all percentages are mole percentages.

2. The feedthrough assembly of claim 1, further comprising at least one terminal pin, wherein the insulating structure comprises a top portion, a bottom portion, and an inner diameter portion, wherein the inner diameter portion defines at least one aperture extending from the top portion to the bottom portion, and wherein the at least one terminal pin extends through the at least one aperture.

3. The feedthrough assembly of claim 2, wherein the glass seal further comprises up to about 10% of $MnO_2$.

4. The feedthrough assembly of claim 2, wherein the glass seal comprises about 30% $B_2O_3$, about 20% CaO, about 20% MgO, about 5% $La_2O_3$, about 10% $SiO_2$, and about 15% $Al_2O_3$.

5. The feedthrough assembly of claim 2, further comprising a second glass seal sealing the at least one terminal pin with the insulating structure.

6. The feedthrough assembly of claim 2, further comprising a gold braze sealing the at least one terminal pin with the insulating structure.

7. The feedthrough assembly of claim 1, wherein the ferrule includes a wall portion and a ledge, the insulating structure abuts the ledge, and the glass seal fixedly secures the insulating structure to the wall portion.

8. The feedthrough assembly of claim 1, wherein the glass seal further comprises up to about 10% of $MnO_2$.

9. The feedthrough assembly of claim 1, wherein the glass seal comprises about 30% $B_2O_3$, about 20% CaO, about 20% MgO, about 5% $La_2O_3$, about 10% $SiO_2$, and about 15% $Al_2O_3$.

10. The feedthrough assembly of claim 1, wherein softening or melting a glass preform forms the glass seal.

11. A method of manufacturing a feedthrough assembly, comprising:
    providing a ferrule;
    inserting an insulating structure within the ferrule; and
    forming a glass seal that fixedly secures the insulating structure within the ferrule, the glass seal comprising:
       about 30% $B_2O_3$;
       about 30% to about 40% of a member selected from the group consisting of CaO, MgO, SrO, and combinations thereof, with the proviso that the individual amounts of CaO and MgO are each not greater than about 20%;
       about 5% $La_2O_3$;
       about 10% $SiO_2$; and
       about 15% $Al_2O_3$,
       wherein all percentages are mole percentages.

12. The method of claim 11, further comprising inserting at least one terminal pin into at least one aperture of the insulating structure, wherein the insulating structure comprises a top portion, a bottom portion, and an inner diameter portion, and wherein the inner diameter portion defines the at least one aperture that extends from the top portion to the bottom portion.

13. The method of claim 12, wherein the glass seal further comprises up to about 10% of $MnO_2$.

14. The method of claim 12, wherein the glass seal comprises about 30% $B_2O_3$, about 20% CaO, about 20% MgO, about 5% $La_2O_3$, about 10% $SiO_2$, and about 15% $Al_2O_3$.

15. The method of claim 12, further comprising forming a second glass seal that seals the at least one terminal pin with the insulating structure.

16. The method of claim 12, further comprising forming a gold braze seal that seals the at least one terminal pin with the insulating structure.

17. The method of claim 11, wherein the ferrule includes a wall portion and a ledge, the insulating structure abuts the ledge, and the glass seal fixedly secures the insulating structure to the wall portion.

18. The method of claim 11, wherein the glass seal further comprises up to about 10% of $MnO_2$.

19. The method of claim 11, wherein the glass seal comprises about 30% $B_2O_3$, about 20% CaO, about 20% MgO, about 5% $La_2O_3$, about 10% $SiO_2$, and about 15% $Al_2O_3$.

20. The method of claim 11, wherein forming the glass seal that fixedly secures the insulating structure within the ferrule comprises softening or melting a glass preform.

21. A feedthrough assembly, comprising:
    a ferrule;
    an insulating structure comprising a top portion, a bottom portion, and an inner diameter portion, wherein the inner diameter portion defines at least one aperture extending from the top portion to the bottom portion;
    at least one terminal pin extending through the at least one aperture; and
    a glass seal fixedly securing the at least one terminal pin with the insulating structure, the glass seal comprising:
       about 30% $B_2O_3$;
       about 30% to about 40% of a member selected from the group consisting of CaO, MgO, SrO, and combinations thereof, with the proviso that the individual amounts of CaO and MgO are each not greater than about 20%;
       about 5% $La_2O_3$;
       about 10% $SiO_2$; and
       about 15% $Al_2O_3$,
       wherein all percentages are mole percentages.

22. The feedthrough assembly of claim 21, wherein the glass seal further comprises up to about 10% of $MnO_2$.

23. The feedthrough assembly of claim 21, wherein the glass seal comprises about 30% $B_2O_3$, about 20% CaO, about 20% MgO, about 5% $La_2O_3$, about 10% $SiO_2$, and about 15% $Al_2O_3$.

24. The feedthrough assembly of claim 21, further comprising a second glass seal fixedly securing the insulating structure within the ferrule.

25. The feedthrough assembly of claim 24, wherein the second glass seal comprises:
- about 30% $B_2O_3$;
- about 30% to about 40% of a member selected from the group consisting of CaO, MgO, SrO, and combinations thereof, with the proviso that the individual amounts of CaO and MgO are each not greater than about 20%;
- about 5% $La_2O_3$;
- about 10% $SiO_2$; and
- about 15% $Al_2O_3$, wherein all percentages are mole percentages.

26. The feedthrough assembly of claim 25, wherein the second glass seal further comprises up to about 10% of $MnO_2$.

27. The feedthrough assembly of claim 25, wherein the second glass seal comprises about 30% $B_2O_3$, about 20% CaO, about 20% MgO, about 5% $La_2O_3$, about 10% $SiO_2$, and about 15% $Al_2O_3$.

28. The feedthrough assembly of claim 24, wherein the ferrule includes a wall portion and a ledge, the insulating structure abuts the ledge, and the second glass seal fixedly secures the insulating structure to the wall portion.

29. The feedthrough assembly of claim 21, further comprising a gold braze fixedly securing the insulating structure within the ferrule.

30. The feedthrough assembly of claim 21, wherein softening or melting a glass preform forms the glass seal.

* * * * *